(12) United States Patent
McMurtry et al.

(10) Patent No.: US 7,463,996 B2
(45) Date of Patent: Dec. 9, 2008

(54) METHOD AND APPARATUS FOR SCANNING

(75) Inventors: David Roberts McMurtry, Dursley (GB); Peter John Wells, Minchinhampton (GB)

(73) Assignee: Renishaw PLC, Gloucestershire (GB)

( * ) Notice: Subject to any disclaimer, the term of this patent is extended or adjusted under 35 U.S.C. 154(b) by 162 days.

(21) Appl. No.: 10/577,480

(22) PCT Filed: Nov. 24, 2004

(86) PCT No.: PCT/GB2004/004953

§ 371 (c)(1),
(2), (4) Date: Apr. 27, 2006

(87) PCT Pub. No.: WO2005/054781

PCT Pub. Date: Jun. 16, 2005

(65) Prior Publication Data

US 2007/0081201 A1    Apr. 12, 2007

(30) Foreign Application Priority Data

Nov. 28, 2003   (GB)   ................................. 0327698.7

(51) Int. Cl.
*G01B 15/00* (2006.01)
*G01B 20/00* (2006.01)
*G06F 15/00* (2006.01)

(52) U.S. Cl. ..................................................... 702/155
(58) Field of Classification Search .................. 702/155
See application file for complete search history.

(56) References Cited

U.S. PATENT DOCUMENTS

| | | | | |
|---|---|---|---|---|
| 4,901,256 A | * | 2/1990 | McMurtry et al. | 702/168 |
| 5,088,046 A | * | 2/1992 | McMurtry | 700/161 |
| 5,373,222 A | * | 12/1994 | Hemmerle et al. | 318/652 |
| 5,384,663 A | | 1/1995 | Garrett et al. | |
| 5,607,305 A | * | 3/1997 | Andersson et al. | 433/223 |
| 5,733,126 A | * | 3/1998 | Andersson et al. | 433/223 |
| 5,884,239 A | * | 3/1999 | Romanik, Jr. | 702/150 |
| 2005/0028617 A1 | * | 2/2005 | Wells et al. | 73/864.91 |
| 2006/0037208 A1 | * | 2/2006 | McMurtry | 33/554 |
| 2006/0102833 A1 | * | 5/2006 | Eiff et al. | 250/234 |

FOREIGN PATENT DOCUMENTS

| | | |
|---|---|---|
| EP | 0 634 150 A1 | 1/1995 |
| WO | WO 02/28309  * | 4/2002 |
| WO | WO 02/28309 A1 | 4/2002 |
| WO | WO 03/046412 A1 | 6/2003 |
| WO | WO 03/062740 A1 | 7/2003 |

* cited by examiner

*Primary Examiner*—Michael P. Nghiem
*Assistant Examiner*—Cindy H Khuu
(74) *Attorney, Agent, or Firm*—Oliff & Berridge, PLC

(57) ABSTRACT

Disclosed is a scanner for the scanning of articles including a scanning apparatus (10) having a scanning device (18) and a rotatable sample mount (14,420) whereby, the scanning device and mount are relatively displaceable along the rotary axis (48) of the mount, a receptacle (40,140,240,400) mounted on the sample mount, the receptacle being capable of securely accommodating an article (30), and an actuator (146,246) for linearly displacing the receptacle whereby, actuation of the actuator displaces the receptacle and any article secured thereto, with respect to the sample mount. The article may be elongate and the displacement by the actuator is along an axis defined by the elongate axis of the elongate article. Also disclosed is a method of scanning.

22 Claims, 7 Drawing Sheets

METHOD AND APPARATUS FOR SCANNING

Figure 1:
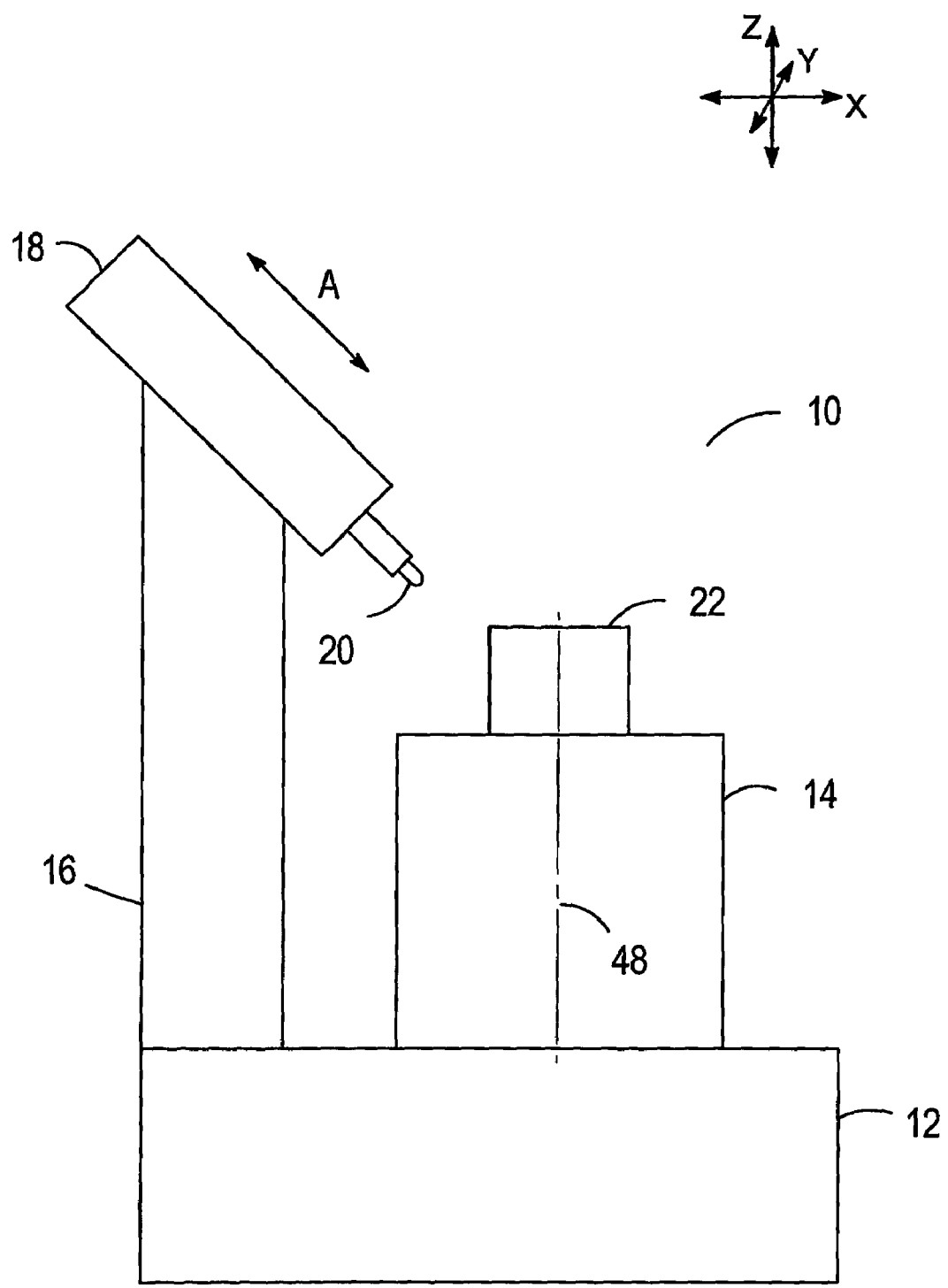

This invention relates to a method and apparatus for scanning and in particular for the scanning of elongated objects such as dental bridges.

Conventionally three-dimensional elongate forms are scanned by following a predetermined path from a starting point to an end point. Depending on the format of the path, deviations in height may be accommodated, however undercuts or recesses which are larger than the sensing tip of the scanning equipment will not be properly mapped. This may also be the case where the elongate form is composed of a number of discrete parts as a sensing tip will not be able to access the intersecting parts of these discrete parts properly.

Where undercuts or recesses are encountered, it is known to provide a circular or helical scan of the object. The object is rotated, the probe may be angled to the axis of rotation and the object manipulated such that no undercuts are presented to the probe or, the probe may be provided with more degrees of freedom so any undercuts can be investigated.

If there is a size consideration which constrains the working area of a probe, then a circular or helical scan is preferable however currently, this limits the shape of objects that can be scanned.

The present invention allows for the scanning of elongate forms and in particular forms which are composed of (or can be divided into) a number of discrete parts.

According to a first aspect, the present invention provides a method of scanning comprising the steps of:
  providing a scanning apparatus having a scanning device and a rotatable sample mount whereby the scanning device and mount are relatively displaceable along the rotary axis of the mount;
  locating an article on the sample mount such that a first part of the article is scannable by the scanning device;
  scanning the first part of the article;
  relatively displacing the article with respect to the scanning device whereby a second part of the article is scannable;
  noting the relative displacement between the article and the scanning device; and
  scanning the second part.

Preferably, an article is secured to a receptacle prior to being located on the sample mount. In a preferred embodiment, the receptacle is mounted with respect to a slide prior to being located on the sample mount.

Advantageously, the article is composed of at least two separate parts whereby during the scanning of the first part, a second part is removed from the receptacle. This enables a complete scan to be made in the event of undercuts or recesses particularly where the at least two parts are adjacent.

According to a second aspect, the invention provides a scanner for the scanning of articles comprising:
  a scanning apparatus having a scanning device and a rotatable sample mount whereby, the scanning device and mount are relatively displaceable along the rotary axis of the mount;
  a receptacle mounted on the sample mount, the receptacle being capable of securely accommodating an article; and
  an actuator for linearly displacing the receptacle whereby, actuation of the actuator displaces the receptacle and any article secured thereto, with respect to the sample mount.

Preferably, the article is elongate and the displacement by the actuator is along an axis defined by the elongate axis of the elongate article. The elongate axis of the article may be linear or arcuate.

Figure 2:
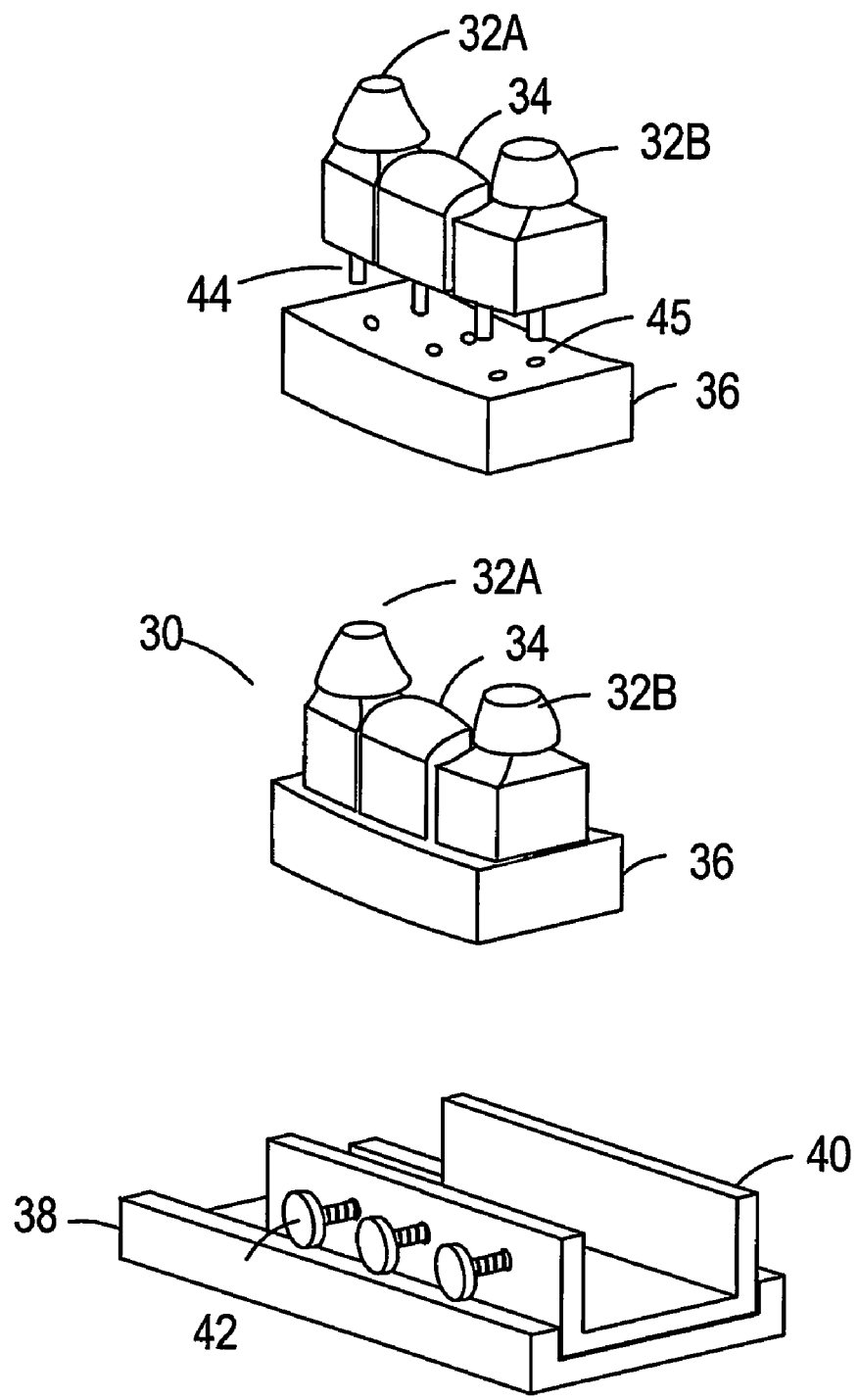
Figure 3:
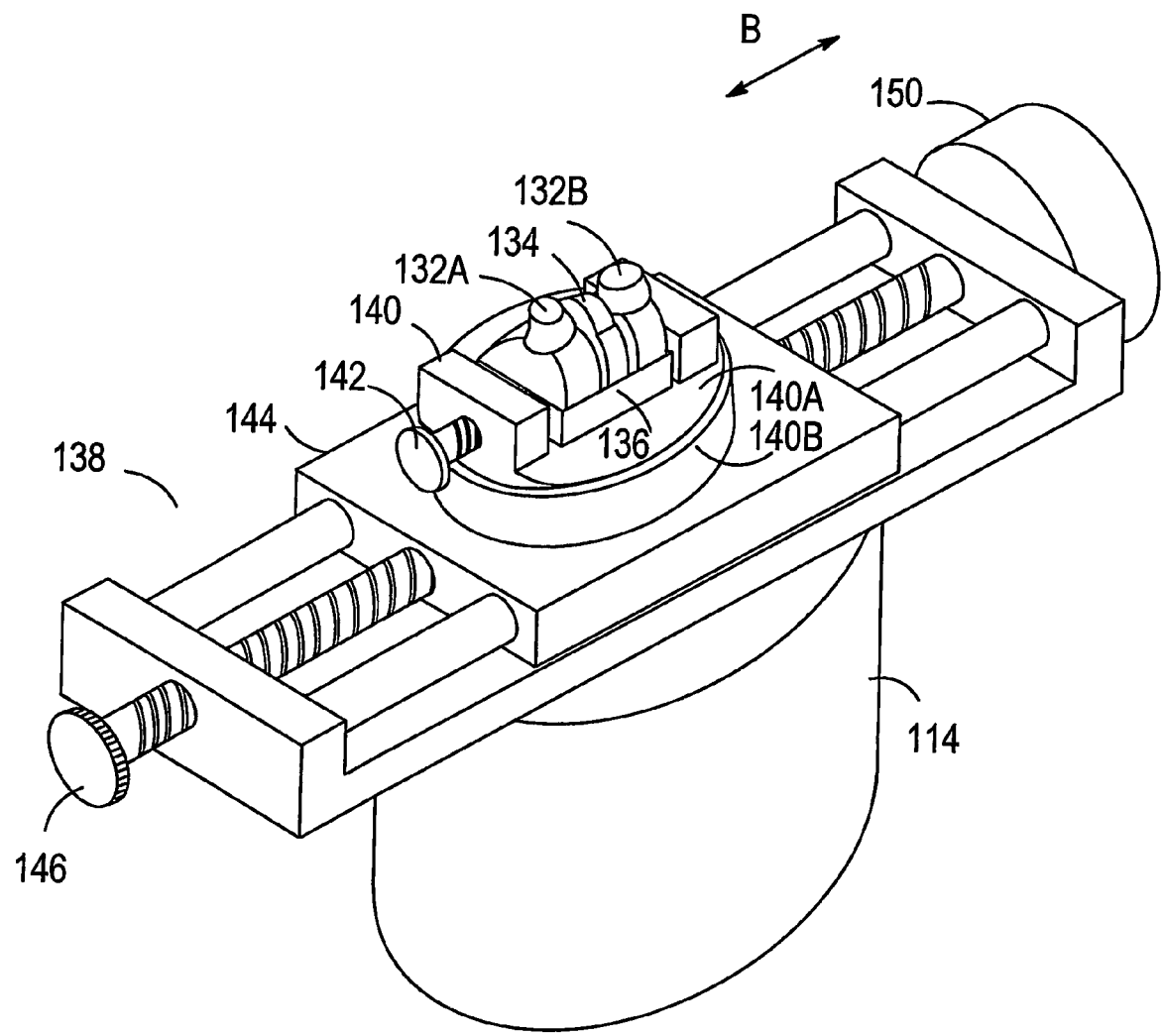
Figure 4:
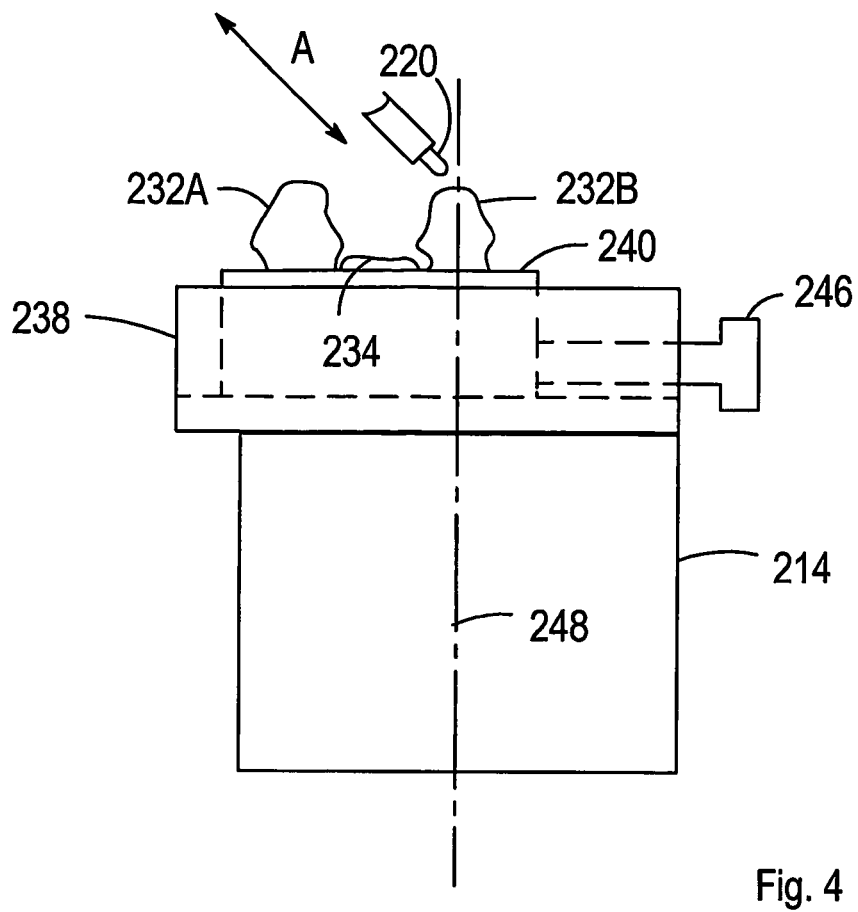
Figure 6:
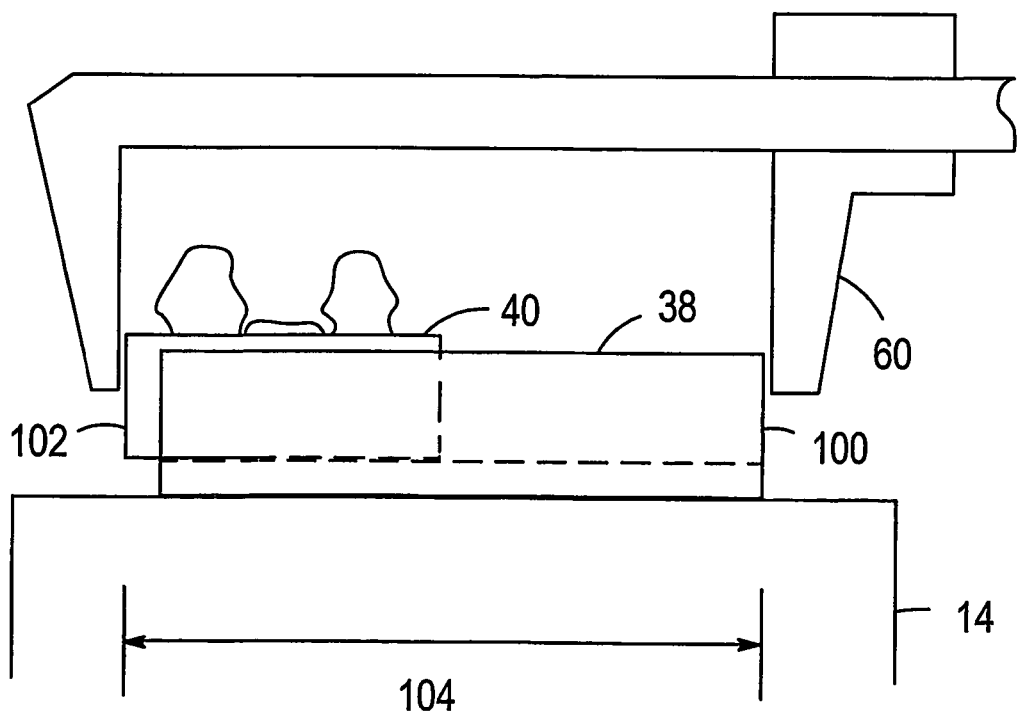
Figure 5B:
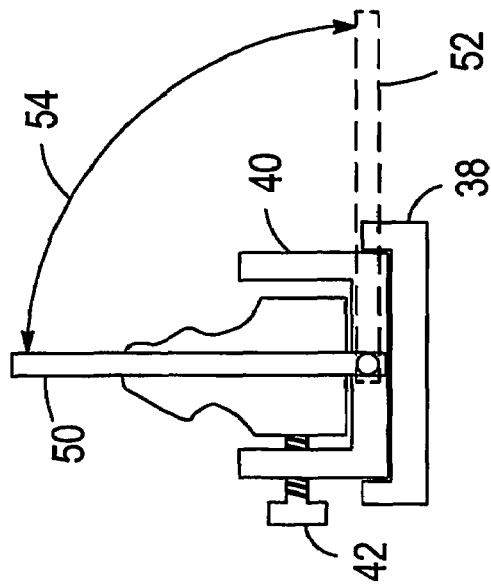
Figure 5A:
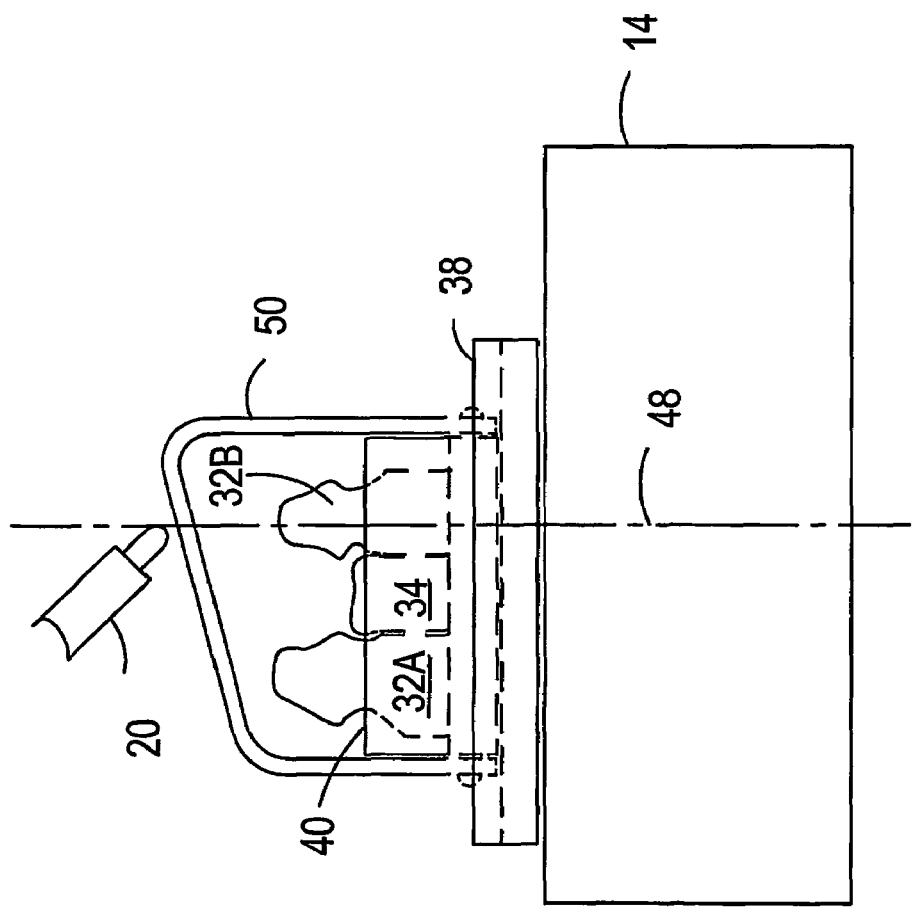
Figure 7A:
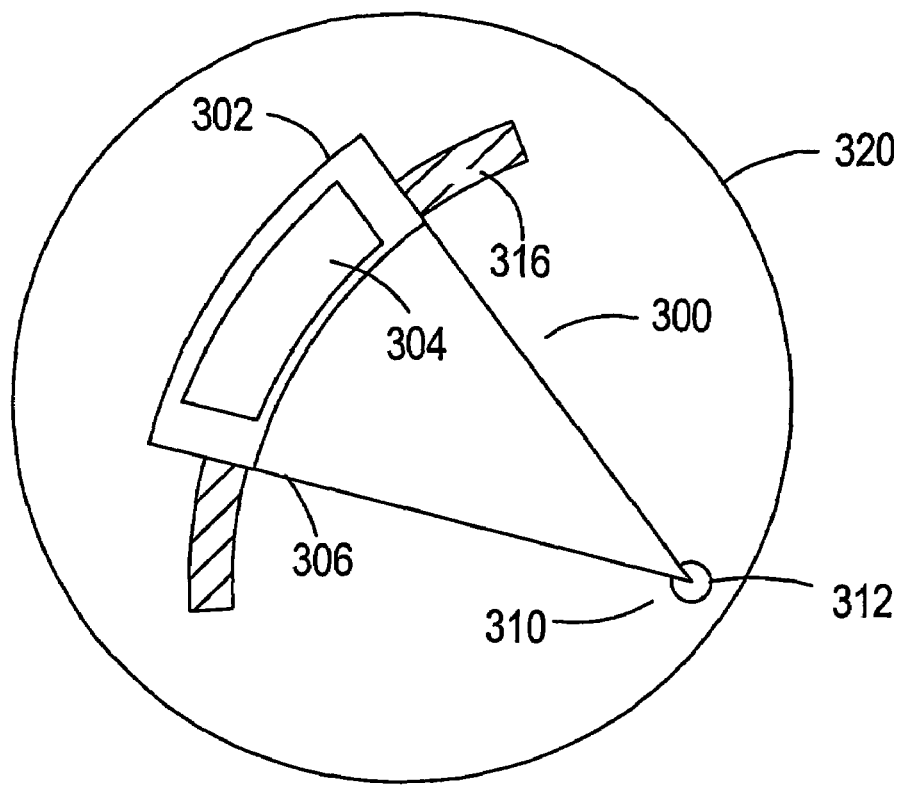
Figure 7B:
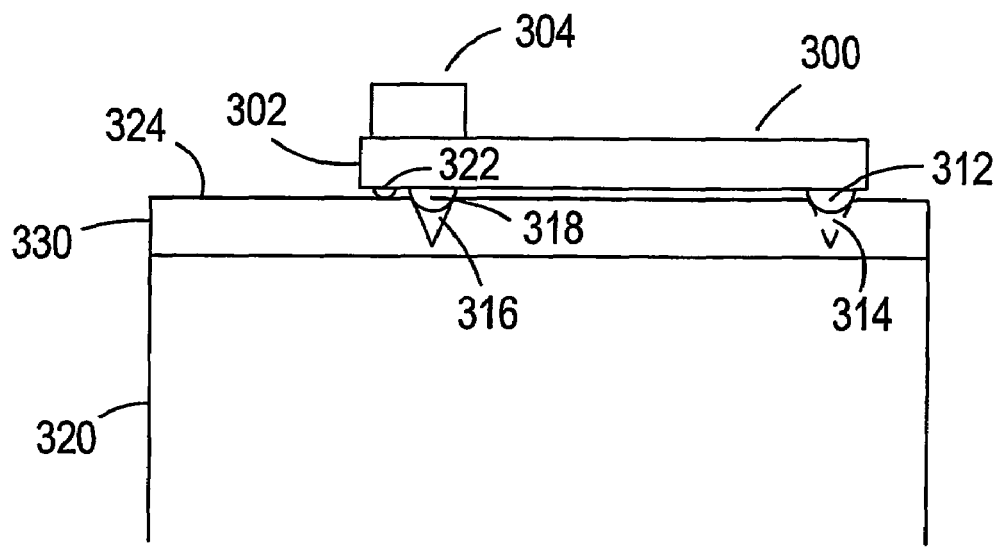
Figure 8:
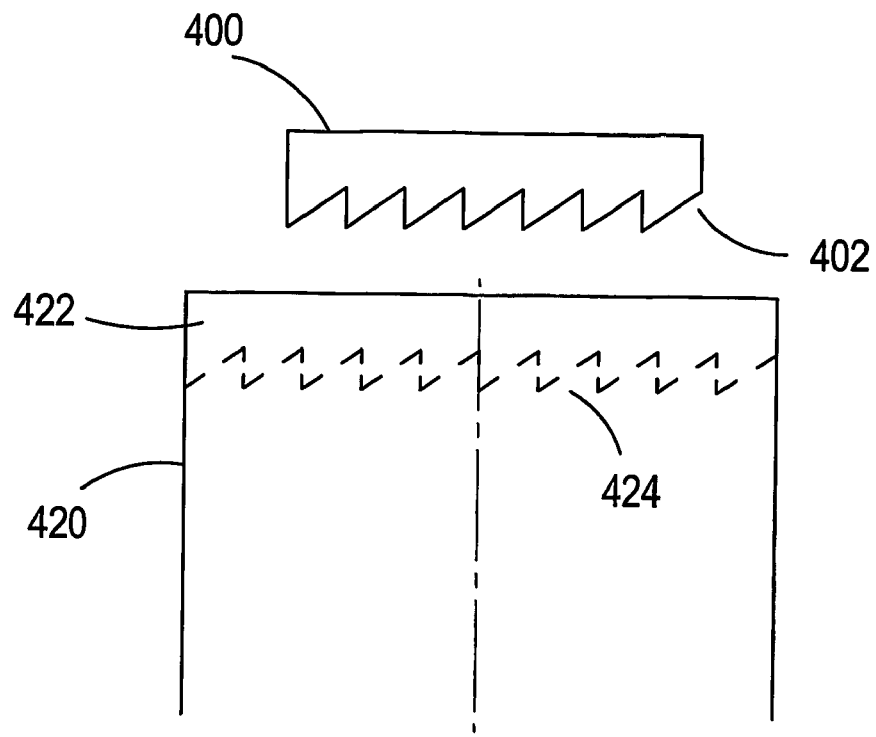
Figure 9:
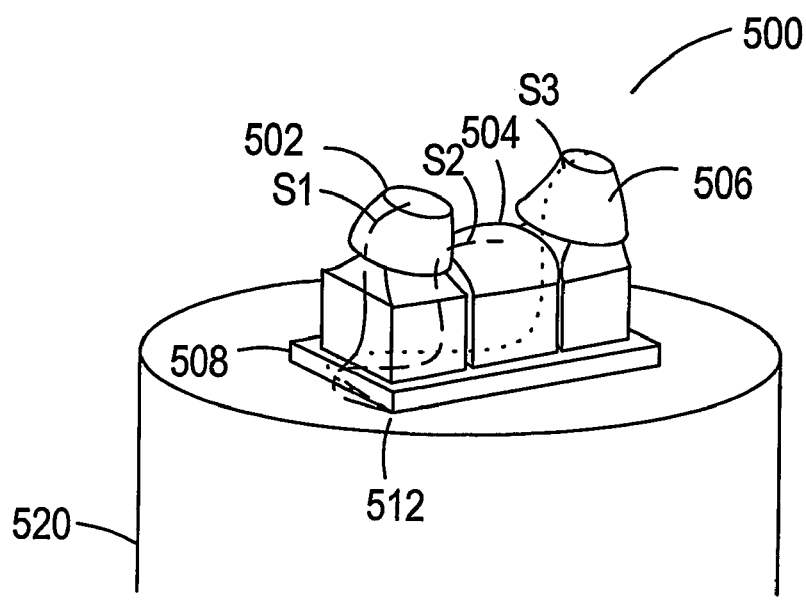

The invention will now be described by way of example and with reference to the accompanying drawings of which:
  FIG. 1 shows a scanning system;
  FIG. 2 shows, in perspective, a receptacle for an article to be scanned;
  FIG. 3 shows, in perspective, an alternative receptacle;
  FIG. 4 shows a receptacle located on a sample mount;
  FIGS. 5a and 5b show a measurement feature whereby the location of the receptacle with respect to the rotational axis of the sample mount and the probe can be determined;
  FIG. 6 shows an alternative measurement device;
  FIGS. 7a and 7b show plan and cross-section views respectively of an alternative receptacle;
  FIG. 8 is a cross-section through a receptacle and co-operating sample mount; and
  FIG. 9 illustrates an embodiment of the invention.

FIG. 1 shows a scanning system 10 having a base 12 onto which a sample holder or mount 14 is rotatably mounted about an axis 48. The base 12 also has a stand 16 which supports a probe 18 having a sensing tip 20. A sample 22 is located on the rotatable sample holder 14.

The sensing tip 20 is movable along an axis A which is inclined to the axis of rotation 48 of the sample holder 14. As the sample holder 14 rotates the sensing tip 20 moves along axis A in response to changes in distance to the sample surface. The sample 22 may be scanned by a series of two-dimensional slices or the sample holder 14 may be rotated at the same time as relative displacement between the probe 18 and the sample holder 14 occurs which produces a helical scan. The probe and/or the sample holder may produce the relative displacement by moving along the Z axis.

An example of a scanning system is described in more detail in WO03/046412 which is herein incorporated by reference. A non contact scanning system may be used with the invention in place of a contact scanning system.

FIG. 2 shows a receptacle 40 for retaining an article 30 which in this case is a part of a model cast from a jaw impression made from, in this example, plaster. The receptacle 40 has securing means 42 which in this case comprises three screws which fix the article 30 in place within the receptacle 40.

The article 30 comprises a base 36 onto which are located bridge supports 32A, 32B and the pontic or missing tooth which is to be bridged 34. The different parts 32A, 32B, 34 of the article are located within the base using locating pins 44 which communicate with respective holes 45 in the base 36. The different parts 32A, 32B, 34 of the article 30 have been separated by, for example, sawing through the plaster model. It is preferred that this process is carried out after the article 30 has been located in the base 36 using locating pins 44 as this will then ensure that the correct spatial relationship between the different parts is retained. Separation of the different parts 32A, 32B, 34 of the article 30 enables parts which are not being scanned to be removed so they do not interfere with the scanning of the remaining part.

Thus, a full scan of each section of the bridge can be completed whilst maintaining the spatial relationship between the different parts thus ensuring that the resultant bridge will fit.

The receptacle 40 is shown mounted within a slide 38. This enables the receptacle 40 and article 30 secured thereto to be moved linearly with respect to the slide. Thus when the slide is located on a sample holder the relative orientation between the receptacle 40, the sample holder and sensing tip of the scanning system is maintained. The slide also facilitates recording of the movement of the receptacle with respect to a sample holder which identifies the distance between each part of the article and enables reproduction of the complete scan for production of the final bridge.

The article 30 need not be located on a base 36, it could be located directly within the receptacle 40. In this situation if it is necessary to remove the redundant parts of the article in order to get a complete scan of the part which is to be scanned and to maintain the spatial relationship between the different parts then, the different parts 32A,32B,34 should be initially secured to the receptacle 40 as a single component. Once this is done they can be separated by for example sawing through the plaster. As the parts are made of plaster and the securing means 42 comprises individual screws for each part, each plaster part will have been marked during the securing process by its screw. Thus the parts can be removed and replaced as required by aligning the marks.

FIG. 3 shows an alternative receptacle 140 for retaining an article. Receptacle 140 has one screw 142 which acts longitudinally through an article for securing the article therein. In this example, a base 136 is required as each part 132A,132B, 134 of the article 130 is not capable of being individually secured to the receptacle.

The receptacle comprises two halves 140A and 140B which are magnetically attracted but movable relative to each other. This enables angular adjustment of the whole article with respect to a sensing tip (not shown) to reduce the chance of an undercut or recess causing an interruption to a scanning process. Note in order to retain spatial relationship between the parts, this adjustment can only be carried out prior to initiation of the scanning process.

The receptacle 140, is mounted on a slide 138, which comprises a platform 144 mounted on a micrometer screw 146. Actuation of the micrometer screw 146 causes displacement of the platform 144 along axis B. The slide 138 is placed on a rotatable sample mount 114.

Alternatively, instead of displacing the receptacle, the probe is displaced along the X-axis (see FIG. 1). This method is not preferred as it results in parts of an article being scanned when they are not substantially aligned to the rotational axis of the sample mount 48.

FIG. 4 shows a receptacle 240 which has been mounted in a slide 238 and located on a rotatable sample holder 214. An actuator 246 has been provided to move the receptacle 240 and thus the article to be scanned with respect to the slide 238 and the sample holder 214.

A scan is conducted as follows. The first tooth 232B is approximately centred on the rotational axis 248 of the sample holder 214. The two parts 232A,234 of the bridge which are not being scanned at this moment are removed from the receptacle 240 by pulling them out of the base (not shown). The first part 232B is scanned.

The second part 234 is replaced within the base and the first part 232B removed. The receptacle 240 is moved with respect to the slide 238 using actuator 246 until the second part 234 is aligned on the rotational axis 248 of the sample holder 214. The second part 234 is now scanned using the sensing tip 220. The third part 232A of the bridge is now replaced in the base within the receptacle 240 and the second part 234 removed from the base. The receptacle 240 is again moved with respect to the slide 238 using actuator 236 until the third part 232A is aligned on the axis of rotation 248 of the sample holder 14. The third part of the scan is then carried out.

The relationship between the receptacle and rotational axis of the sample holder is established in FIG. 3 by the micrometer screw 146. Thus by noting the reading of the micrometer screw, when each part is aligned to the rotational axis of the sample holder, the distance between the centre-point of each scan section is known and can be used to build a composite scan of the whole article which has the correct spatial relationships between the different scans and so teeth. Note, this can be carried out before or after a part is scanned. Thus, the receptacle is re-datumed after each movement to any position with respect to the slide.

In reality, it is the spatial relationship between the different teeth that is required, but as the teeth are temporarily fixed in location with respect to the slide, a measure of slide position is equivalent.

It is important that when the measurements of the position of the receptacle 240 with respect to the axis of rotation 248 are taken when the receptacle is co-planar to the axis of movement A of the probe and the axis of rotation 248 because this ensures that any measured distance between the centre of rotation of each part scan is a true measurement. Basically, the longitudinal axis B of the receptacle is aligned with respect to axes A and 248 so the orientation of the receptacle with respect to axes A and 248 is the same for each measurement.

If the receptacle 240 were not co-planar to the axes A and 248 then the spatial relationship between the parts 232A, 232B,234 of the article would be distorted (as a diagonal measurement would have been taken). One way to ensure that the receptacle 240 is co-planar to the axes A and 248 when each of the relative measurements are taken, is described below referring to FIG. 1. When the receptacle 40 is initially lined up as co-planar to the axes A and 48, a mark is made on the side of the sample holder near its point of interception with the base 12 of the scanning system. A second mark cooperating is made on the base 12. When the first scan has been completed and it is time to move the receptacle 40 with respect to the slide 38 to align the second part 34 onto the axis of rotation 48 of the sample holder 14, the marks on the sample holder 14 and base 12 are re-aligned thus ensuring that the receptacle 40 is again normal to the probe axis A. Alternatively the sample holder 14 can be provided with a permanent mark located adjacent base 12 and the base 12 could comprise a series of marks around the circumference of the sample mount and for each scanning process the position of alignment (when the receptacle 40 is co-planar to the axes A and 48) could be indicated by for example a sticker which is positioned next to the mark on the base which corresponded to the mark on the sample holder 14 when aligned.

Alternatively holder 14 could be driven about the axis of rotation 48 by a motor and encoder with a fixed reference mark. Calibration of the relative angles of the axes of motion and the reference mark permit the adjustment of the receptacle 40 along axis B to be carried out with the holder 14 in any orientation with respect to the base 12 or axis A.

Although the parts of the article have been aligned to the rotational axis of the sample holder, this is a preferred feature for some embodiments of the invention. Having an item aligned on the rotational axis makes the interpretation of data from a scan easier and ensures that the transducer in the probe is not used near its limits of motion.

FIGS. 5a and 5b show a measurement feature 50 which can be used to determine the relative positions of the different parts of the article during their respective scans. FIG. 5a shows the angled feature 50 when being used to establish the location of the receptacle 40 with respect to the axis of rotation 48 of the sample holder 14. FIG. 5b shows the angled feature 50 in its retracted position 52.

The angled feature 50 is rotatably mounted to the receptacle 40 and has a gradient with respect to the length of the receptacle 40. Thus moving from one end of the receptacle 40 to the other results in the distance from the receptacle 40 to the angled feature 50 changing. When a part 32B of the article 30 is correctly located on the rotational axis 48, the probe tip 20 is brought into contact with the angled feature 50. The angled feature 50 is then retracted by rotating it through 90° (shown in FIG. 5b) and the first part of the scan carried out as described previously. When the second part 34 of the article 30 is subsequently aligned to the rotational axis 48 the probe tip is again brought to the angled feature 50. As there is a gradient on the angled feature the position of the probe tip 20 along axis A of the probe will be different. The gradient of the angled feature is known so the distance between the centre point of the first and the second parts of the scan is also known.

FIG. 6 shows an alternative measurement device which is a set of Vernier callipers 60. In this example, the distance between one end 100 of the slide 38 and the distal end 102 of the receptacle 40 is measured to obtain relative positions of each part of the article for the different scans. The Vernier callipers 60 are not attached to the system and are removed once a measurement 104 has been taken.

The measurement of the distances between the centre of rotation for each part scan can be carried out in a number of ways. When the movement with respect to the rotary axis is manually controlled, a Vernier scale on the moving part (receptacle 40, FIG. 2, or platform 144, FIG. 3), a micrometer screw or external Vernier callipers are preferred methods.

When the movement with respect to the rotary axis is controlled using a motor i.e. automatically, an encoder system (linear or rotary) having a scale and a readhead is preferred. A motorised movement can be achieved in a number of ways an external electric signal can be passed to the moving part via slip rings or contacts at one orientation of the device; an inductive or capacitive couple at one orientation; a motor could be attached to the device, for example 150 in FIG. 3; or the device could be battery operated and controlled by radio or optical signals.

While adjustment of the receptacle 48 along one axis B (see FIG. 3) accommodates simple parts, it may be required to provide 2 orthogonal axes of adjustment to scan more than two bridge supports on a base 36.

FIGS. 7a and 7b show plan and cross-sectional views respectively of an alternative receptacle according to the invention. In this embodiment, the receptacle 300 is curved reproducing the form of a section of jaw. The receptacle is segment shaped and is repeatably located on the sample holder 320 by five points of contact. A first contact location is at the centre of rotation 310 of the receptacle 300. Second and third contact locations are radially spaced away from the centre of rotation 310 proximate an outer circumference 302 described by the receptacle. An article 304 is disposed on receptacle 300 near the outer circumference 302 such that any individual parts of the article 304 are at approximately the same radius from the centre of rotation i.e. as the receptacle rotates the parts follow each other along the same path.

The centre of rotation 310 is located near the edge of the base 320 in order to maximise movement of an article 304 housed in the receptacle 300 whilst minimising the required diameter of the base 320. The first contact location comprises a ball seated within a cone and comprises three points of contact. The ball 312 is embedded in the lower surface of the receptacle 300 and is seated within a cone shaped hole 314 in the upper surface of the base 302. The receptacle movement describes an arc about this first contact location.

Second and third contact locations are disposed near the outer circumference 302 of the receptacle. The second and third contact locations comprise single points of contact between the upper surface of the base 320 and a ball 322 embedded in the lower surface of the receptacle 300. The second and third contact locations are disposed one at each radial edge of the segment shaped receptacle so the three contact locations describe a triangle.

Alternatively the first contact could be arranged as described and the second and third contact locations comprise two points of contact in each formed by a 'v'-shaped curved groove 316 machined in the upper surface of the base 320 and a second ball 318 embedded in the underside of the receptacle 300. The groove 316 is part of a circle having a centre at the same point as the centre of rotation of the receptacle In order to scan an article, a first part of the article is positioned with respect to a probe (not shown). To establish the relative locations of different parts of the article, one radial edge 306 of the receptacle is located and its co-ordinates stored. The first part of the article is scanned. The receptacle is rotated to position a second part of the article with respect to the probe. The new co-ordinates of the radial edge 306 of the receptacle are established and the second part is scanned. This process is repeated until all the parts of the article have been scanned. The relative position of each scan part with the radial edge of the receptacle enables a composite image of the whole article to be generated graphically.

The movement of the receptacle may be executed by a manual process, or motorised.

As an alternative, the 'v'-shaped groove 316 is replaced with a plurality of discrete 'v' notches machined into the surface of the base. In this embodiment, the notches are of known relationship thus, as the receptacle is indexed between each notch, so long as the notch location of the receptacle is known, it is no longer necessary to locate the edge of the receptacle prior to scanning each part as the relative location of the receptacle is already known.

Instead of the balls being embedded in the underside of the receptacle, they may be embedded in the upper surface of the base. Additionally, rather than disrupting the flat surface of a base, a mount 330 may be provided which attaches to the base by, for example a magnetic attraction.

FIG. 8 is a cross-section through a receptacle 400 and co-operating sample mount 420. The receptacle has a plurality of gear teeth 402 machined into a surface and the sample mount 420 has a central trench 422 which accommodates (at least partially) the receptacle 400. The base of the trench 422 includes a set of mating gear teeth 424 which co-operate with the gear teeth 402 of the receptacle 400. The receptacle may be manually or mechanically (for example by a motor) moved with respect to the sample mount 420.

The gear teeth are accurately machined so the distance moved by the receptacle 400 as it engages an adjacent gear tooth is known thus, counting the number of gear teeth moved between scan parts enables the scan parts to be matched together. Thus, there are a plurality of defined or index positions.

Alternatively, the gear teeth are merely used to engage the receptacle and the sample mount. In this case, a scale may be provided enabling receptacle position with respect to the sample mount to be read or, the probe is used to establish the distance between the edge of the receptacle and the tooth.

FIG. 9 shows an article 510 comprising three parts 502, 504,506 mounted on a base 508 and placed on a sample mount 520. In this embodiment, it is not the article 510 which is moved between scan parts, but the probe (not shown).

The parts 504,506 which are not being scanned are removed from the base 508 and the remaining part is scanned by a probe. At the end of the scan, the probe is moved S1 to a designated corner 512 of the base 508 and the displacement of the probe tip between the end of the scan and the corner 512 of the base 508 is recorded. The same process is repeated after the middle 504 and other end 506 parts of the article are scanned giving two further displacements S2, S3 respectively between the middle 504 and other end 506 parts and the designated corner 512 of the base. In this example, the end of each scan is shown as being when the probe reaches the top of the tooth or pontic however, this is a matter of choice. As long as the relationship between the last piece of scanned data and the designated corner is known, the individual parts of the whole scan can be joined electronically to produce a composite scan.

The reference point for each scan part need not be a designated corner of a base. It may alternatively be a point on the surface of the sample mount. If a diameter of the sample mount through which all the parts of the article lie can be accurately located by the scanning device, then the positions of each part of the article along this diameter can be established in order to facilitate the combining of the different scan parts into a composite representation.

The next important stage in the production of replacement teeth is establishing what the external shape should be. The conventional way of doing this is by using a waxed-up model. A layer of wax is applied to the plaster model and shaped until the supporting teeth and missing tooth have been re-built (it may be necessary to check the re-build against abutting teeth on the opposing jaw to ensure accuracy).

Once satisfied with the wax model, the individual parts of the article are re-scanned using the method described herein thus providing data regarding the shape of the outer surface of the bridge. This data is then used to manufacture the bridge in conjunction with the data from the first set of part scans (which give the size and shape of the internal surface of the bridge).

The invention claimed is:

1. A method of scanning comprising the steps of:
providing a scanning apparatus having a scanning device and a rotatable sample mount, the mount and at least a portion of the scanning device being relatively linearly displaceable in a direction toward and away from an article held by the mount in a direction parallel to a rotary axis of the mount, wherein, when the mount is rotated, a slice scan of the article is produced and, when the mount is rotated and the scanning device and mount are relatively displaced by movement in the direction parallel to the rotary axis, a helical scan of the article is produced;
locating the article on the sample mount such that a first part of the article is scannable by the scanning device;
scanning the first part of the article;
relatively displacing the article with respect to the scanning device whereby a second part of the article is scannable;
noting the relative displacement between the article and the scanning device; and
scanning the second part.

2. A method according to claim 1, wherein the article is secured to a receptacle.

3. A method according to claim 2, wherein the receptacle is mounted with respect to a slide.

4. A method according to claim 1, wherein the article is composed of at least two separate parts whereby during the scanning of the first part, a second part is removed from the receptacle.

5. A scanner for the scanning of articles comprising:
a scanning apparatus having a scanning device and a rotatable sample mount, the mount and the scanning device being relatively linearly displaceable in a direction toward and away from an article mounted on the rotatable sample mount in a direction parallel to a rotary axis of the mount, wherein, when the mount is rotated, a slice scan of the article is produced and, when the mount is rotated and the scanning device and mount are relatively displaced by movement in the direction parallel to the rotary axis, a helical scan of the article is produced;
a receptacle mounted on the sample mount, the receptacle being capable of securely accommodating an article; and
an actuator for linearly displacing the receptacle whereby, actuation of the actuator displaces the receptacle and any article secured thereto, with respect to the sample mount.

6. A scanner according to claim 5, wherein the article is elongate and the displacement by the actuator is along an axis defined by the elongate axis of the elongate article.

7. A scanner according to claim 5, wherein the actuator is a micrometer.

8. A scanner according to claim 5, including a measurement feature which measures relative positions of different parts of the article.

9. A scanner according to claim 8, wherein the measurement feature is a micrometer or a set of Vernier calipers.

10. A scanner according to claim 5, wherein the actuator is manual.

11. A scanner according to claim 5, wherein the actuator is automatic.

12. A scanner according to claim 5, wherein the receptacle has a plurality of defined positions with respect to the sample mount.

13. A scanner according to claim 5, wherein the receptacle has a plurality of defined positions with respect to the sample mount.

14. A scanner for the scanning of articles comprising:
a scanning apparatus having a scanning device and a rotatable sample mount, the mount and the scanning device being relatively linearly displaceable in a direction toward and away from an article mounted on the rotatable sample mount, by movement in a direction parallel to a rotary axis of the mount, wherein, when the mount is rotated, a slice scan of the article is produced and, when the mount is rotated and the scanning device and mount are relatively displaced by movement in the direction parallel to the rotary axis, a helical scan of the article is produced;
a receptacle mounted on the sample mount, the receptacle being capable of securely accommodating an article; and
an actuator for displacing the receptacle, whereby actuation of the actuator displaces the receptacle and any article secured thereto, with respect to the sample mount.

15. A scanner according to claim 14, wherein the article is elongate and the displacement by the actuator is along an axis defined by the elongate axis of the elongate article.

16. A scanner according to claim 14, wherein the actuator is manual.

17. A scanner according to claim 14, wherein the actuator is automatic.

18. A scanner for the scanning of articles comprising:
a scanning apparatus having a scanning device and a rotatable sample mount, the mount and the scanning device being relatively linearly displaceable in a direction toward and away from an article mounted on the rotatable sample mount in a direction parallel to a rotary axis of the mount, wherein, when the mount is rotated, a slice scan of the article is produced and, when the mount is rotated and the scanning device and mount are relatively displaced by movement in the direction parallel to the rotary axis, a helical scan of the article is produced, a receptacle mounted on the sample mount, the receptacle being capable of securely accommodating an article; and means for displacing the receptacle with respect to the sample mount.

19. A scanner according to claim 18, wherein the article is elongate and the displacement by the actuator is along an axis defined by the elongate axis of the elongate article.

20. A scanner according to claim 18, wherein the actuator is manual.

21. A scanner according to claim 18, wherein the actuator is automatic.

22. A scanner according to claim 18, wherein the receptacle has a plurality of defined positions with respect to the sample mount.

* * * * *

UNITED STATES PATENT AND TRADEMARK OFFICE
CERTIFICATE OF CORRECTION

PATENT NO.        : 7,463,996 B2
APPLICATION NO. : 10/577480
DATED             : December 9, 2008
INVENTOR(S)       : David Roberts McMurtry and Peter John Wells Page 1 of 1

It is certified that error appears in the above-identified patent and that said Letters Patent is hereby corrected as shown below:

Col. 8, line 29,
Please replace claim 13 with the following claim 13:

13. A scanner according to claim 14, wherein the receptacle has a plurality of defined positions with respect to the sample mount.

Signed and Sealed this

Seventeenth Day of March, 2009

JOHN DOLL
*Acting Director of the United States Patent and Trademark Office*